United States Patent

Sussman

[11] 4,033,679
[45] July 5, 1977

[54] GONIOSCOPE

[76] Inventor: Walter Sussman, 2260 Merrick Road, Merrick, N.Y. 11566

[22] Filed: Dec. 10, 1975

[21] Appl. No.: 639,532

[52] U.S. Cl. .................................. 351/16; 351/1; 351/6; 351/15; 350/96 R
[51] Int. Cl.² .......................................... A61B 3/10
[58] Field of Search ............... 351/1, 6, 10, 15, 16, 351/26, 174, 159, 7; 350/199, 201, 202, 175 E, 190, 96 R

[56] References Cited

UNITED STATES PATENTS

| | | | |
|---|---|---|---|
| 2,430,851 | 11/1947 | Allen | 351/1 |
| 3,413,067 | 11/1968 | Froio | 350/96 R X |
| 3,452,589 | 7/1969 | Hargen et al. | 351/1 |
| 3,589,800 | 6/1971 | Cardona | 351/1 |
| 3,675,984 | 7/1972 | Vulmiere | 350/96 R |
| 3,820,879 | 6/1974 | Frisen | 351/15 |

FOREIGN PATENTS OR APPLICATIONS

| | | | |
|---|---|---|---|
| 227,868 | 11/1962 | Australia | 351/1 |
| 782,295 | 9/1957 | United Kingdom | 351/15 |

*Primary Examiner*—Saxfield Chatmon, Jr.
*Attorney, Agent, or Firm*—Allison C. Collard

[57] ABSTRACT

A gonioscope for viewing the angle of the trabeculum and the drainage angle and related structures comprising a lens having a cylindrical surface and formed at its front end with four inclined facets narrowing toward the front free end thereof. The lens includes a front surface substantially perpendicular to the longitudinal axis of the cylinder having therein a concave inwardly directed recess, the said facets constituting total internal reflection surfaces.

10 Claims, 3 Drawing Figures

GONIOSCOPE

The present invention relates to a gonioscope.

A gonioscope (i.e., a gonioprism or goniolens) is an instrument applied to the front of the eye (cornea), so that the drainage angle (trabeculum, trabecular area and related structures) can be viewed. This is essential in the diagnosis of certain types of glaucoma, some tumors, or other eye disorders and is used in cooperation with a separate viewing-illuminating system, of which a slit lamp is the most common, or a special unit (which is suspended from the ceiling) or an ophthalmoscope. Most of the commonly used devices require a fluid or jelly which is placed between the cornea and the contact area. This constitutes a drawback with such devices.

Rays of light reflecting from certain internal portions of the eye such as the anterior ciliary body, the peripheral iris and others cannot be seen by a trained and skilled observer like an ophthalmologist without the use of an optical instrument. These rays strike the cornea of the eye at a critical angle and undergo complete internal reflection. In order for these rays to be seen, the corneal curve must be neutralized or changed by means of contact lenses. Thus, every thorough eye examination, especially when there is an indication of presence of eye disease, requires the use of some sort of diagnostic contact lens. In addition, certain kinds of diagnostic contact lenses are essential to accurate eye surgery.

One type of lens useful in work of this nature is commonly referred to as a direct viewing gonioscopic contact lens. A lens of this type permits the rays of light to be observed directly by the examiner instead of being completely internally reflected back into the eye. A slit lamp is usually used in conjunction with a gonioscopic contact lens to help in studying the configuration of the angles.

Various designs of direct viewing gonioscopic contact lenses have been used in the past to view internal rays of light reflected from within the eye. However, these structures have not proven entirely satisfactory for various reasons, e.g., the lens has remained difficult to manipulate on the eye, has required an additional instrument or attachment to hold it in place, and has allowed annoying air bubbles to frequently form between the lens and cornea.

One known device has a large applied surface and requires fluid as a coupling medium and has a mirror embedded in plastic which is hand-held and requires rotation. Another is known, having a small application surface and does not require fluid. However, this device is usually used with a separate metal forceps which is somewhat clumsy and has four mirrors of silvered glass. Problems develop with this device, such that the glass chips, and that the silvering of the mirrors wears off, and the device is somewhat clumsy. Another device with four mirrors and made of plastic is known.

This device is delicate and hard to insert. Still another device has a lens without a prism or mirror and a very large contact area and requires fluid and an overhead viewing-illumination system.

It is an object of the present invention to provide an improved gonioscope, avoiding the disadvantages of the prior art, and without requiring the use of fluids to be placed in the eye prior to contact by the gonioscope.

It is another object of the present invention to provide an improved gonioscope which is simple in construction, excellent in use and inexpensive to manufacture.

In accordance with the present invention there is provided an improved gonioscope constructed of a single piece of plastic material preferably Lucite, and includes four facets constituting total internal reflecting mirrors which surround a small concave contact area.

The instrument in accordance with the present invention is large enough to be held in the hand very easily without a forceps yet has a contact area small enough to use without fluid or jelly, and includes the advantageous features of the presently available commercial units without the accompanying disadvantages thereof.

Other objects and features of the present invention will become apparent from the following detailed description when taken in connection with the accompanying drawings which disclose several embodiments of the invention. It is to be understood that the drawings are designed for the purposes of illustration only, and are not intended as a definition of the limits and scope of the invention disclosed.

In the drawings, wherein similar reference numerals denote similar elements throughout the several views.

Figure 1:
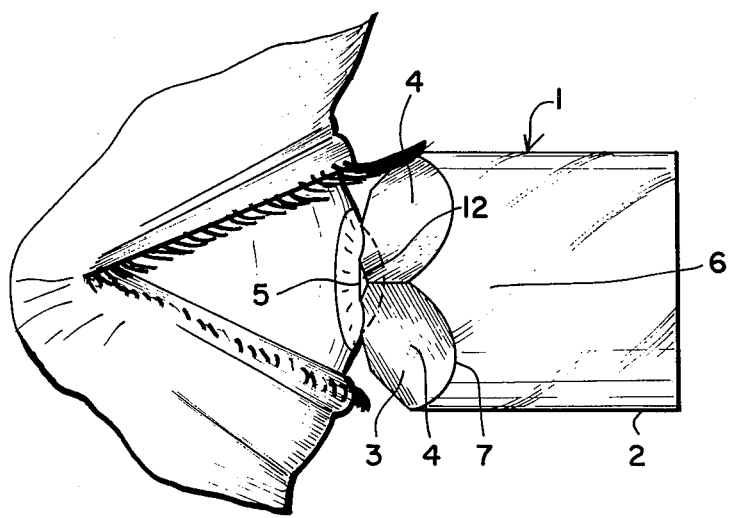
FIG. 1 is a side view of the gonioscope in accordance with the present invention in an operative use position against the cornea of the eye.
Figure 2:
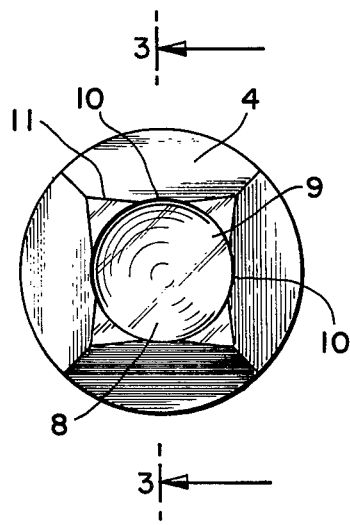
FIG. 2 is a front view of the gonioscope of the present invention.
Figure 3:
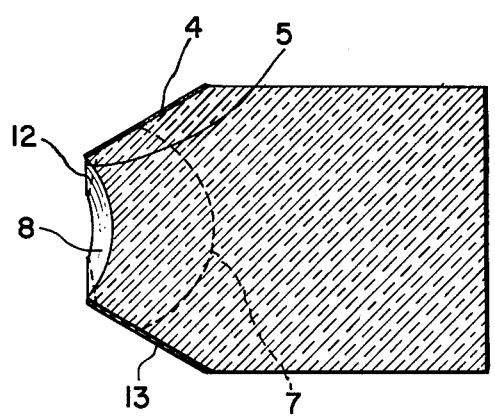
FIG. 3 is a section taken along the lines 3—3 of FIG. 2.

Referring now to the drawing, and more particularly to FIGS. 1–3, a gonioscope 1 in accordance with the present invention is made of a single piece of plastic material, preferably Lucite, which is clear for optical viewing purposes and preferably formed as a solid cylinder 2 having a front portion 3. The front portion is cut into four planar inclined surfaces or facets 4 which extend from the periphery of the cylinder 3 narrowing in a forward direction toward the free end 5. The facets 4 are formed equally spaced about the longitudinal axis 6 of the cylinder in substantially 90° sections thereof and intersect each other at substantially 90° angles, also intersecting the periphery of the cylinder 2 in curved intersections lines 7. In this formation, opposite pairs of the facets 4 are formed symmetrically. The angle of inclination of the planes 4 with respect to the longitudinal axis 6 is less than 45° substantially between 20° and 40°, although not limited thereto, the exact degree being determined so as to provide total internal optical reflection, i.e., at the critical angle thereof for the particular material and wave lengths used. Thus the facets 4 constitute internal reflecting surfaces for reflection of light to and from the eye respectively, of a person when the gonioscope is placed against the cornea as shown in FIG. 1.

The center of the front surface of the unit is formed with a concave recess 8 designed to the curve of the average eyeball, which is applied to the cornea. The edge 9 of the recess 8 is substantially tangential to the front edges 11 of the facets or inclined reflecting surfaces 4 at tangential points 10.

There is provided by the present invention, a small contact area, and the instrument is large enough to be hand-held easily and of plastic construction. It does not require any fluid for application has the advantage of quick viewability, so that the drainage angle can be readily examined.

The facets or inclined surfaces act as reflection surfaces as a result of their inclination, with respect to the particular material of the gonioscope. That is, the facets are designed to at least at the total internal reflection angle, or critical angle, such that it provides total internal reflection. A coating 15 can be applied on the outside on at least the four facets surfaces 3, as an aid for the total internal reflection. Many reflecting coatings which are well known may be used for this purpose, and for this reason are not necessary to be described. It is also preferable to coat the cylindrical surfaces.

In operation, the lens unit is pressed against the eye with the center concave surface against the cornea. Through the unit the drainage angle of the anterior chamber may be viewed. The light comes from a source (not shown) of the instrument, through the lens unit and is reflected at one of the reflecting facets, then passing through the concave recess 8 into the cornea of the eye through the cornea to the anterior chamber, then being reflected back thereto and again through the concave recess 8, again being reflected by the facet and then through the instrument and magnification units (not shown) to the eye of the examiner. The reflection surfaces keeps light from passing through the surfaces of the instrument.

Another variation of this lens that might be useful involves changing the radius of curvature of the surface 8 being applied to the cornea. In some eyes the corneal curvature is substantially different from the average. In such an instance, it is conceivable that a gonioscope with a different front measurement may be preferable.

While only one embodiment of the present invention has been shown and described, it will be obvious that many changes and modifications may be made thereunto without departing from the spirit and scope of the invention.

What is claimed is:
1. A gonioscope for viewing the angle of the trabeculum of the drainage angle comprising:
a lens having a cylindrical surface and being formed at its front end with four inclined facets narrowing toward the front free end thereof,
said facets being inclined substantially between 20° and 45° relative to said longitudinal axis, and having a front surface substantially perpendicular to the longitudinal axis of said cylindrical surface having therein a concave inwardly directed recess,
said facets constituting total internal reflection surfaces.
2. The gonioscope as recited in claim 1, wherein:
said facets are coated with a mirror-type coating substance to aid the total internal reflection.
3. The gonioscope as recited in claim 2 wherein:
said facets are substantially symmetric in size and position to one another relative to said cylindrical surface.
4. The gonioscope as recited in claim 3 wherein:
said facets have front edges which are all aligned substantially in a plane perpendicular to said longitudinal axis of the unit; and
said concave recess has front edges substantially tangential to the front edges of said facets.
5. The gonioscope as recited in claim 2 wherein said cylindrical surface is also coated with a mirror type coating.
6. A gonioscope for viewing the angle of the trabeculum of the drainage angle comprising:
a lens having a cylindrical surface and being formed at its front end with four inclined facets in the external surface of said lens toward the front free end thereof, and having a front surface substantially perpendicular to the longitudinal axis of said cylindrical surface having therein a concave inwardly directed recess, said facets constituting total internal reflection surfaces.
7. The gonioscope as recited in claim 6 wherein said facets are inclined substantially between 20° and 40° relative to said longitudinal axis.
8. The gonioscope as recited in claim 6 wherein:
said facets are substantially symmetric in size and position to one another relative to said cylindrical surface,
said facets being in substantially 90° sections thereof and intersecting each other at substantially 90° angles.
9. The gonioscope as recited in claim 8, wherein:
said facets and said cylindrical surface are coated with a mirror-type coating substance to said total internal reflection.
10. The gonioscope as recited in claim 6 wherein:
said facets have front edges which are all aligned substantially in a plane perpendicular to said longitudinal axis of the unit, and
said front edges being tangential to said internal reflecting surfaces.

* * * * *